United States Patent [19]

Shimizu et al.

[11] Patent Number: 5,650,092
[45] Date of Patent: Jul. 22, 1997

[54] SILACYCLOHEXANE COMPOUNDS, A LIQUID CRYSTAL COMPOSITION COMPRISING THE SAME AND A LIQUID CRYSTAL DEVICE COMPRISING THE COMPOSITION

[75] Inventors: Takaaki Shimizu; Takeshi Kinsho; Tsutomu Ogihara; Tatsushi Kaneko; Mutsuo Nakashima, all of Niigata-ken; Hideshi Kurihara, Kawasaki, all of Japan

[73] Assignee: Shin-Etsu Chemical Co., Ltd., Tokyo, Japan

[21] Appl. No.: 545,889

[22] Filed: Oct. 20, 1995

[30] Foreign Application Priority Data

Oct. 20, 1994 [JP] Japan .................. 6-282740

[51] Int. Cl.$^6$ .................. C09K 19/34; C09K 19/52; C07F 7/08
[52] U.S. Cl. .................. 252/299.61; 252/299.5; 556/406
[58] Field of Search .................. 252/299.61; 556/406

[56] References Cited

U.S. PATENT DOCUMENTS

| | | | |
|---|---|---|---|
| 4,985,565 | 1/1991 | Baney et al. | 548/110 |
| 5,498,737 | 3/1996 | Shimizu et al. | 556/406 |
| 5,545,977 | 8/1996 | Shimizu et al. | 252/299.61 |
| 5,547,606 | 8/1996 | Kinsho et al. | 252/299.61 |

FOREIGN PATENT DOCUMENTS

| | | |
|---|---|---|
| 0 355008 | 2/1990 | European Pat. Off. . |
| 0 657460 | 6/1995 | European Pat. Off. . |
| 3 317921 | 12/1983 | Germany . |
| 60-50177 | 11/1985 | Japan . |
| 60-52744 | 11/1985 | Japan . |
| 61-21937 | 5/1986 | Japan . |
| 1-50691 | 10/1989 | Japan . |
| 1-50693 | 10/1989 | Japan . |
| 1-50694 | 10/1989 | Japan . |
| 3-9895 | 2/1994 | Japan . |

*Primary Examiner*—C. H. Kelly
*Attorney, Agent, or Firm*—Lowe, Price, LeBlanc & Becker

[57] ABSTRACT

A silacyclohexane compound of the following formula (I)

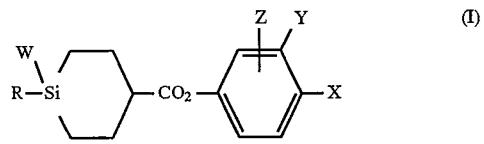

wherein R is an unsubstituted or substituted organic residue, W is H, F, Cl or methyl, X is CN, F, Cl or an unsubstituted or substituted organic residue, and Y and Z independently represent H, F or Cl. The silacyclohexane compounds are useful in liquid crystal compositions and also in liquid crystal devices.

8 Claims, No Drawings

SILACYCLOHEXANE COMPOUNDS, A LIQUID CRYSTAL COMPOSITION COMPRISING THE SAME AND A LIQUID CRYSTAL DEVICE COMPRISING THE COMPOSITION

BACKGROUND OF THE INVENTION

1. Field of the Invention

This invention relates to a novel silacyclohexane compound. The invention also relates to a liquid crystal composition composing the silacyclohexane compound and to a deuce composing the composition.

2. Description of the Prior Art

The liquid crystal display devices make use of optical anisotropy and dielectric anisotrophy of liquid crystal substances. Depending on the mode of display, a variety of display systems are known including those of a twisted nematic type (TN type), a supertwisted nematic type (STN type), a super birefringence the (SBE type), a dynamic scattering type (DS type), a guest/host type, a the of deformation of aligned phase (DS type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the the of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all the requirements have never been known when used singly. In practice, several to ten and several liquid compounds and/or latent liquid crystal compounds are mixed to provide a liquid crystal mixture. To this end, it is important that constituent components be readily compatible with one another.

Among these constituent components, compounds having ring structures of phenyl cyclohexanecarboxylates of the following formulas are known as having a relatively low viscosity and capable of decreasing a threshold voltage.

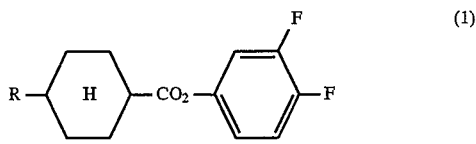

(1)

wherein R represents an alkyl group having from 1 to 9 carbon atoms as set out in Japanese Patent Publication No. 61-21937.

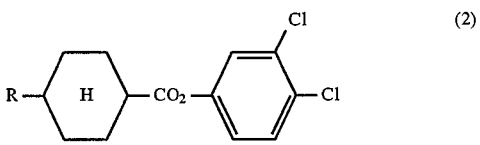

(2)

wherein R represents an alkyl group having from 1 to 10 carbon atoms as set out in Japanese Patent Publication No. 1-50691.

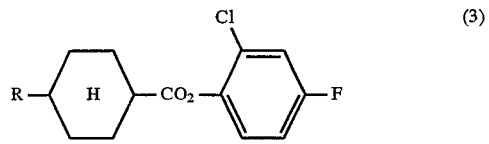

(3)

wherein R represents an alkyl group from 1 to 10 carbon atoms as set out in Japanese Patent Publication No. 1-50693.

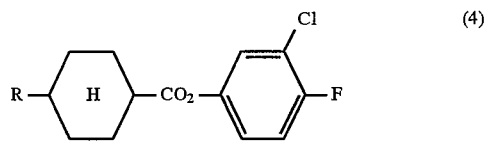

(4)

wherein R is an alkyl group having from 1 to 10 carbon atoms as set out in Japanese Patent Publication No. 1-50694.

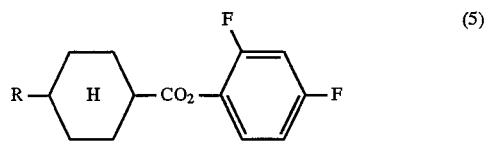

(5)

wherein R is an alkyl group having from 1 to 10 carbon atoms as set out in Japanese Patent Publication No. 3-9895.

Moreover, known compounds whose dielectric anisotropy, $\Delta\epsilon$, is negative are ones mentioned below.

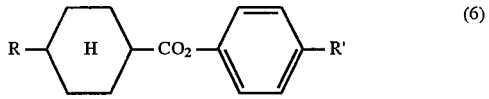

(6)

wherein R and R' are, respectively, an alkyl group having from 4 to 7 carbon atoms as set out in Japanese Patent Publication No. 60-50177.

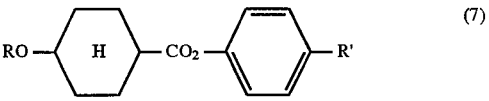

(7)

wherein R and R' are, respectively, an alkyl group having from 1 to 10 carbon atoms as set out in Japanese Patent Publication No. 60-52744.

As the liquid crystal display devices recently have wider utility, the characteristic properties required for the liquid crystal materials become severer. In particular, the high performance characteristics of the materials have now been demanded owing to the requirements for high response speed and function in portableness. In order to realize the high speed response, liquid crystal compositions should have low viscosity. For the portability, limitation is inevitably placed on a power supply, so that it is necessary that the drive voltage be low or the power consumption be low, i.e. the liquid crystal composition used be low in threshold voltage. On the other hand, in multiplex drive systems wherein a high contrast is essentially required, threshold characteristics should be sharp or the dielectric constant ratio between the dielectric anisotropy, $\Delta\epsilon$, and the dielectric constant along a minor axis, $\epsilon\perp$, should be small. Most liquid crystal compounds have a dielectric anisotropy, $\Delta\epsilon$, which is a positive value or is close to zero. In order to reduce the dielectric constant ratio of a mixed composition of the compounds, liquid crystal compounds whose value of Δε is negative are necessary.

SUMMARY OF THE INVENTION

It is an object of the invention to provide a novel compound which is able to lower a viscosity and a threshold voltage when used at least as one of constituent components of a liquid crystal composition.

It is another object of the invention to provide a novel compound serving as a liquid crystal substance which has a silacyclohexane ring containing a silicon atom in a molecular structure.

It is a further object of the invention to provide a liquid crystal composition which comprises at least one compound of the type as set out above and also a liquid crystal display device comprising the composition.

The above object can be achieved, according to the invention, by a silacyclohexane compound of the following formula (I)

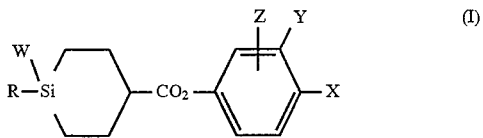

wherein R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms, or an alkenyl group having from 2 to 8 carbon atoms, W represents H, F, Cl or $CH_3$, X represents CN, F, Cl, $CF_3$, $OCF_3$, $OCF_2Cl$, $OCHFCl$, $OCHF_2$, a linear alkyl group or alkoxy group each having from 1 to 10 carbon atoms, an alkoxyalkoxy group having from 2 to 7 carbon atoms, $(O)_lCY_1=CX_1X_2$ wherein l is 0 or 1, $Y_1$ and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl, and Y and Z, respectively, represent H, F or Cl.

According to the invention, there is also provided a liquid crystal composition which comprises the silacyclohexane compound of the type mentioned above along with a liquid crystal display device which comprises the composition.

DETAILED DESCRIPTION OF THE INVENTION

The novel compounds of the invention serving as a liquid crystal substance have a trans-silacyclohexane ring structure and are of the formula (I)

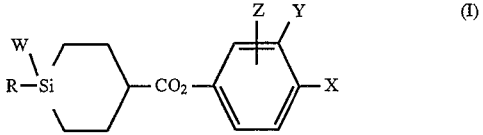

In the formula (I), R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms, or an alkenyl group having from 2 to 8 carbon atoms.

Specific examples of the linear alkyl group having from 1 to 10 carbon represented by R include methyl, ethyl, n-propyl, n-butyl, n-pentyl, n-hexyl, n-heptyl, n-octyl, n-nonyl and n-decyl.

Specific examples of the branched alkyl group having 3 to 8 carbon atoms include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl and ethoxypentyl.

Specific examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the alkenyl group having from 2 to 8 carbon atoms include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

In the formula, W represents H, F, $C_1$ or $CH_3$.

X represents CN, F, Cl, $CF_3$, $OCF_3$, $OCHF_2$, $OCF_2Cl$, OCHFCl, a linear alkyl group having 1 to 10 carbon atoms, a linear alkoxy group having from 1 to 10 carbon atoms, an alkoxyalkoxy group having from 2 to 7 carbon atoms, $(O)_lCY_1=CX_1X_2$ wherein l is 0 or 1, $Y_1$ and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl. Examples of the linear alkyl group include methyl, ethyl, n-propyl, n-butyl, n-pentyl, n-hexyl, n-heptyl, n-octyl, n-nonyl and n-decyl. Likewise, examples of the linear alkoxy group include methoxy, ethoxy, n-propoxy, n-butoxy, n-pentoxy, n-hexyloxy, n-heptyloxy, n-octyloxy, n-nonyloxy and n-decyloxy. Examples of the alkoxyalkoxy group include methoxymethoxy, ethoxymethoxy, propoxymethoxy, butoxymethoxy, pentoxymethoxy, hexyloxymethoxy, methoxyethoxy, ethoxyethoxy, propoxyethoxy, butoxyethoxy, pentoxyethoxy, methoxypropoxy, ethoxypropoxy, propoxypropoxy, butoxypropoxy, methoxybutoxy, ethoxybutoxy, propoxybutoxy, methoxypentoxy, ethoxypentoxy and methoxyhexyloxy.

Y and Z, respectively, represent H, F or Cl.

The silacyclohexane compound of the afore-indicated formula (I) has the following structural moiety of the following formula (1)

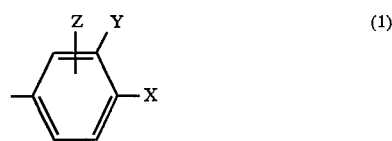
(1)

Specific examples of the moiety include those of the following formulas

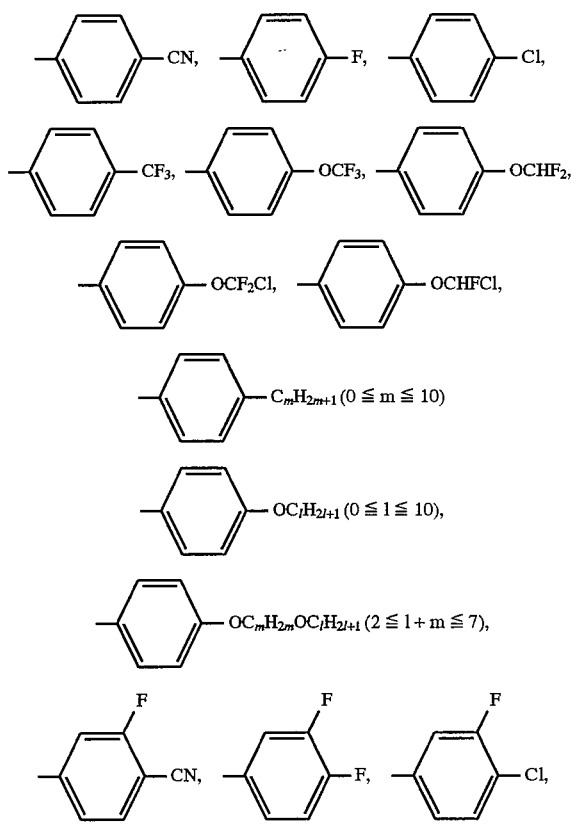

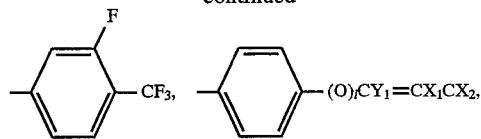

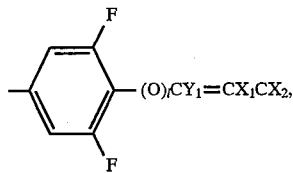

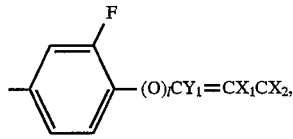

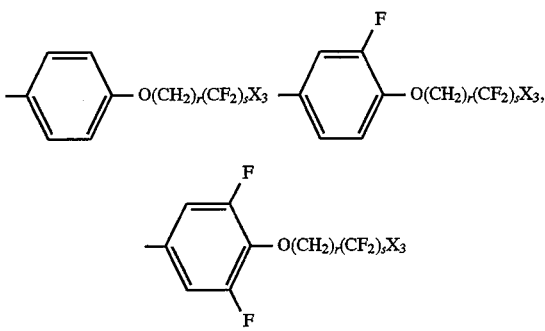

wherein l, $Y_1$, $X_1$, $X_2$, r, s and $X_3$ are, respectively, as defined hereinbefore,

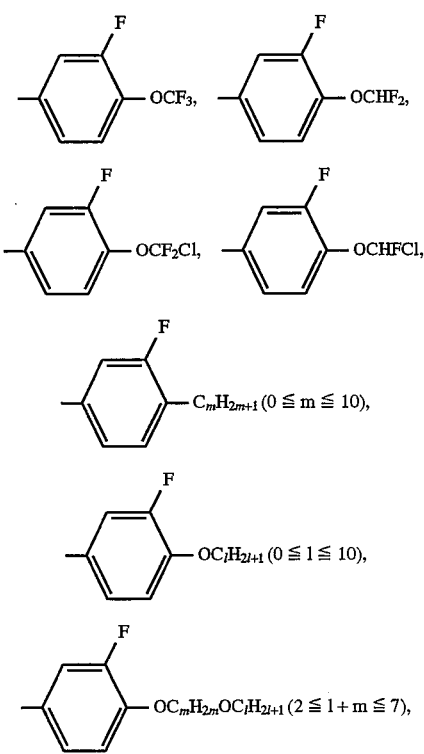

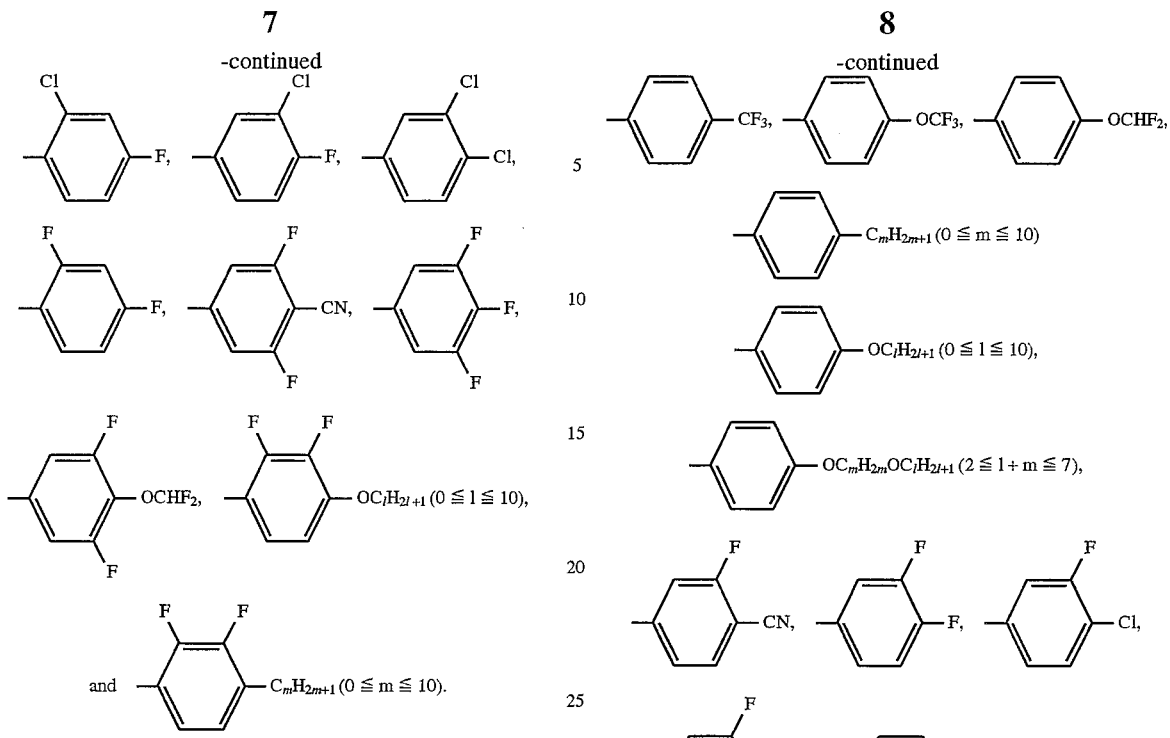

Of these groups or atoms, preferred groups represented by R include: linear alkyl groups having from 2 to 7 carbon atoms, such as ethyl, n-propyl, n-butyl, n-pentyl, n-hexyl and n-heptyl; branched alkyl groups having from 3 to 8 carbon atoms, such as isopropyl, 1-methylpropyl, 2-methylpropyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl, methoxypropyl, methoxypentyl, ethoxymethyl, ethoxyethyl, propoxymethyl and pentoxymethyl; mono or difluoroalkyl groups having from 1 to 10 carbon atoms, such as 2-fluoroethyl, 2-fluoropropyl, 2-fluorobutyl, 4-fluoropentyl, 5-fluoropentyl, 1,1-difluoroethyl, 2,2-difluoroethyl, 2,2-difluoropropyl, 2,2-difluorobutyl, 4,4-difluorobutyl and 4,4-difluoropentyl; and alkenyl groups such as 1-pentenyl group, 3-pentenyl group, 4-pentenyl group, 1-hexenyl group, 5-hexenyl group, 6-heptenyl group and 7-octenyl group.

Preferred atoms or groups represented by W include H, F or $CH_3$.

Preferred moieties represented by the formula (1)

Of these, the compounds having the moieties of the following formulas exhibit a value of $\Delta\epsilon$ close to zero -continued

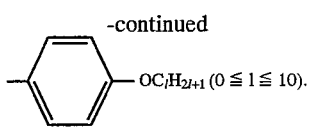

Moreover, the compounds having moieties of the following formulas exhibit a negative value of $\Delta\epsilon$

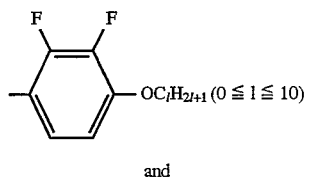

and

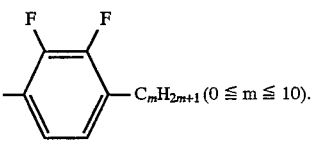

The above-mentioned four compounds are particularly suitable for use in DS type, DAP type or GH (guest-host) type display devices.

The preparation of the silacyclohexane compound of the formula (I) according to the invention is now described. The silacyclohexane compounds of the formula (I) differ in manner of preparation depending on the type of substituent joined to the silicon atom of the silacyclohexane ring.

With the methylsilacyclohexane compounds of the following formula (I) wherein the substituent bonded to the silicon atom of the silacyclohexane ring is a methyl group, i.e. W is a methyl group in the formulas, the compounds are prepared by esterification reaction (i.e. condensation reaction through dehydration) between carboxylic acid compounds of the following general formula (2) and the phenols of the following general formula (3)

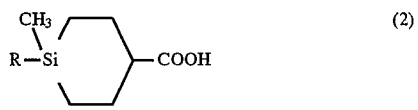

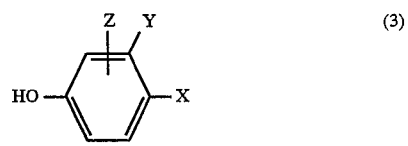

wherein X, Y and Z have, respectively, the same meanings as defined hereinbefore.

The esterification reaction may be carried out by (1) a method wherein the two compounds are condensed by use of dehydrators and (2) a method wherein the carboxylic acid is first converted to an acid chloride and then reacted with the phenol compound in the presence of bases.

The dehydrators used in the method (1) include, for example, diimides such as N,N'-dicyclohexylcarbodiimide, acid anhydrides such as trifluoroacetic anhydride, carbonyldiimidazole, 2-chloropyridinium salts, 3-chloroisooxazolium salts, and combinations of 2,2'-dipyridyldisulfide and phosphines such as methyl phosphine.

In this case, the reaction is preferably effected under conditions of a temperature of from 0° to 100° C. for a time of from 0.5 to 10 hours in a solvent inert to the reaction. Examples of the solvent include carbon tetrachloride, methylene chloride, aromatic hydrocarbons such as benzene, toluene, xylene and the like, and ethers such as tetrahydrofuran.

The reagents used to convert the carboxylic acid to a corresponding acid chloride in the method (2) include thionyl chloride, phosphorus pentachloride, oxalyl chloride, and combinations of carbon tetrachloride and phosphines. This reaction proceeds by a usual manner preferably under conditions of a temperature ranging from 0° to 100° C. The acid chloride is then reacted with the phenol compound in the presence of bases. Examples of the base include pyridine, N,N-dimethylaniline, triethylamine, tetramethylurea and the like. This reaction proceeds readily under normal temperature and pressure conditions.

Moreover, the compounds of the formula (I) wherein W is chlorine, fluorine or hydrogen, (i.e. the atom or substituent joined to the silicon atom of the silacyclohexane ring or rings is chlorine, fluorine or hydrogen), include chlorosilacyclohexane, fluorosilacylohexane and hydrosilacyclohexane compounds. For the preparation of these compounds, arylsilacyclohexane compounds wherein an aryl group such as phenyl or tolyl is attached to the silicon atom of the silacyclohexane ring is used as an intermediate for preparing the chlorosilacyclohexane, fluorosilacylohexane and hydrosilacyclohexane compounds. The arylsilacyclohexane compound is of the general formula (I) wherein W is an aryl group such as phenyl or tolyl.

These arylsilacyclohexane intermediate compounds are prepared through esterification or dehydration and condensation between corresponding carboxylic acids of the following formula (4) and phenol compounds of the above-indicated formula (3), like the compounds of the formula (I) wherein W is CH$_3$

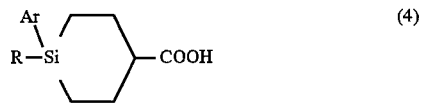

wherein Ar is phenyl or tolyl and R has the same meaning as defined hereinbefore,

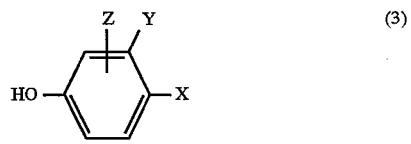

The conversion of the arylsilacyclohexane intermediate compound to an intended chlorosilacyclohexane, fluorosilacylohexane or hydrosilacyclohexane compound is carried out according to the following reaction sequence

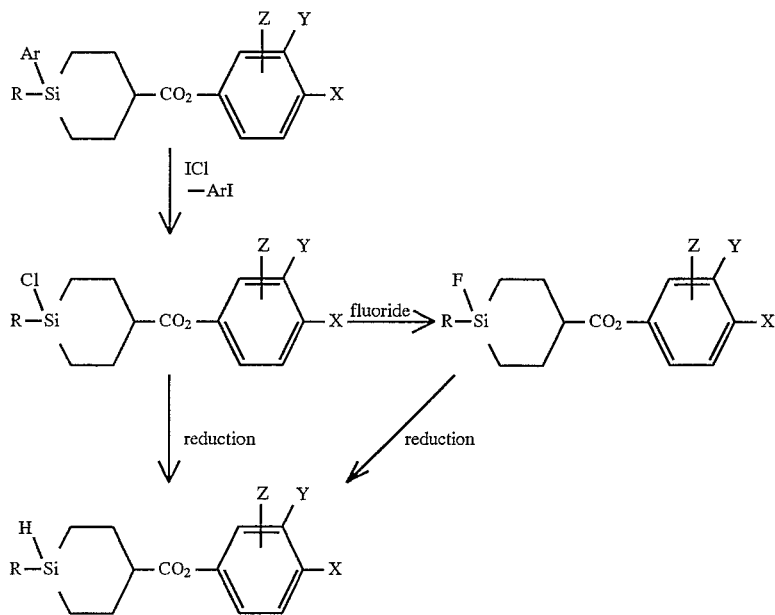

wherein Ar represents a phenyl or tolyl group.

As will be apparent from the above reaction sequence, when iodine monochloride is reacted with the arylsilacyclohexane compound, a chlorosilacyclohexane compound is obtained through the halo de-silylation reaction. The de-silylation reaction may be caused in a wide range of temperatures. Preferably, the temperature used is in the range of from 0° to 80° C., more preferably from 10° to 40° C.

When the resultant chlorosilacyclohexane compound is reacted with fluorides such as cesium fluoride, copper (I) fluoride, antimony fluoride, calcium fluoride, zinc fluoride, tetra-n-butylammonium fluoride and the like, a fluorosilacyclohexane compound of the formula (I) wherein W is fluorine is obtained. The reaction is carried out in a temperature range of from 0 to a boiling point of the system in hydrocarbon solvents such as hexane, heptane, benzene, toluene and the like.

Moreover, when the chlorosilacyclohexane or fluorosilacyclohexane compound is reacted with a reducing agent under mild conditions not permitting the ester to be reduced, a hydrosilacyclohexane compound of the formula (I) wherein W is hydrogen is obtained. Examples of the reducing agent include metal hydrides such as sodium hydride, calcium hydride, trialkylsilanes, boranes, dialkyl alumininm compounds and the like, and complex hydrides such as lithium aluminium hydride, sodium borohydride, lithium borohydride, potassium borohydride, tributylammonium borohydride and the like. Although not limitative, the reduction of the halosilacyclohexane is carried out preferably at a temperature of from −50° to 100° C., more preferably from −20° to 70° C.

If the thus obtained product is in the form of steric isomers, a trans isomer is isolated and purified through known purification procedures such as recrystallization, chromatography and the like.

The silacyclohexane compounds of the invention are appropriately used in combination with known liquid crystal compounds to provide a liquid crystal composition. Such liquid crystal compounds suitable for this purpose include those compounds of the general formulas (6) and (7)

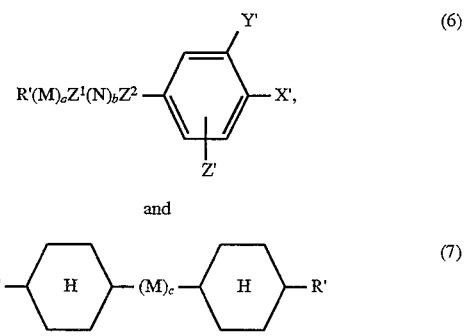

In the above formula (6) and (7), each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms as defined in the afore-indicated formula (I); X' is same as X defined hereinbefore and represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_iCY_1=CX_1X_2$ wherein is 0 or 1, $Y_1$ and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted trans-1,4-cyclohexylene group which has, if substituted, one or more substituents such as F, Cl, Br, CN and an alkyl group having from 1 to 3 carbon atoms, (2) a trans-1,4-cyclohexylene group wherein one $CH_2$ unit or two $CH_2$ units, not adjacent each other, of the cyclohexane ring are replaced by O or S, (3) a 1,4-cyclohexenylene group, (4) an unsubstituted or substituted 1,4-phenylene group having, if substituted, one or two atoms or groups such as F, Cl, $CH_3$ and/or CN group and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, $-CH_2CH_2-$, $-CH=CH-$, $-C\equiv C-$, $-CO_2-$, $-OCO-$, $-CH_2O-$, $-OCH_2-$ or single bond.

In the above formulas (6) and (7), if a and c are both 2, M's may be the same or different and are independently selected from the groups (1) to (5) set forth above, and if b is 2, N's may be the same or different.

The silacyclohexane compounds of the invention which may be used singly or in combination should preferably be present in a liquid crystal phase or composition in an amount of from 1 to 50 mole %, preferably from 5 to 30 mole %. As a matter of course, the liquid crystal composition may further comprise polychromatic dyes capable of forming colored guest-host systems, and additives capable of imparting dielectric anisotropy, viscosity modifiers, additives for changing the direction of alignment of a nematic phase.

In practice, the liquid crystal phase or composition comprising at least one compound of the invention is used as a liquid crystal display device wherein the composition is hermetically sealed between optically transparent substrates each having an electrode of a desired shape. If necessary, the device may have various types of undercoatings, overcoatings for controlling the alignment, polarizers, filters and reflective layers as is known in the art. Alternatively, a multi-layer cell may be used to incorporate the compounds of the invention. The liquid crystal display device may be used in combination with other types of display devices, semiconductor substrates, and light sources.

With the compounds of the invention whose value of $\Delta\epsilon$ is positive or is close to zero, the liquid crystal display device is driven according to a twisted nematic (TN) system, a super twisted nematic (STN) system or a guest-host (GH) system. For the compounds whose value of $\Delta\epsilon$ is negative, a dynamics scattering mode (DSM) system, an electrically controlled birefringence (ECB) system, a guest-host (GH) system and the like known in the art may be adopted.

The invention is more particularly described by way of examples.

EXAMPLE 1

Preparation of (4-chlorophenyl) trans-4-n-heptyl-4-methyl-4-silacyclohexanecarboxylate 21.0 g of N,N'-dicyclohexylcarbodiimide (DCC) was added to a mixture of 25.6 g of trans-4-n-heptyl-4-methyl-4-silacyclohexanecarboxylic acid, 13.5 g of 4-chlorophenol, 14.0 g of 4-dimethylaminopyridine and 350 ml of methylene chloride at room temperature. The resultant reaction mixture was agitated for 8 hours at room temperature, after which the resultant N,N'-dicyclohexyl urea was removed by filtration. The filtrate was washed with brine, dried and concentrated to obtain a residue, followed by silica gel chromatography to obtain 20.1 g (yield: 55%) of the intended product.

EXAMPLE 2

Preparation of (4-trifluoromethoxyphenyl) trans-4-methyl-4-n-pentyl-4-silacyclohexanecarboxylate The general procedure of Example 1 was repeated using trans-4-methyl-4-n-pentyl-4-silacyclohexanecarboxylic acid and 4-trifluoromethoxyphenol, thereby obtaining the intended product.

EXAMPLE 3

Preparation of (4-trifluoromethoxyphenyl) trans-4-n-pentyl-4-silacyclohexanecarboxylate A mixture of 50 g of 4-n-pentyl-4-phenyl-4-silacyclohexanecarboxylic acid, 50.0 g of triphenylphosphine and 420 ml of carbon tetrachloride was agitated under reflux for 1 hour. Then, a mixture of 32.0 g of 4-trifluoromethoxyphenol and 100 ml of pyridine was added to the mixture, followed by further addition of 1.00 g of 4-dimethylaminopyridine and agitation at room temperature for 9 hours. The resultant reaction mixture was poured into dilute hydrochloric acid, followed by extraction with ethyl acetate. The ethyl acetate solution was washed with brine, dried and concentrated, followed by purification of the resultant residue with silica gel chromatography to obtain 60.8 g (yield: 78%) of (4-trifluoromethoxyphenyl) 4-n-pentyl-4-phenyl-4-silacyclohexanecarboxylate. The results of IR and NMR analyses are shown below.

IR (liquid film) $v_{max}$: 2922, 2862, 1759, 1502, 1261, 1184, 1113, 1016, 982, 868 $cm^{-1}$ $^1$H-NMR (CDCl$_3$) δ: 0.7–2.7 (20H, m), 7.0–7.7 (9H, m) ppm 70 ml of a carbon tetrachloride solution of 1.0 mole of iodine monochloride was added to a mixture of 30.0 g of the thus obtained product and 300 ml of carbon tetrachloride at 0° C. and agitated for 12 hours. The reaction mixture was concentrated under reduced pressure to obtain 27.2 g (quantitative yield) of (4-trifluoromethoxyphenyl) 4-chloro-4-n-pentyl-4-silacyclohexanecarboxylate. The results of gas chromatography-mass spectroscopy (GC-MS) are shown below.

GC-MS (m/z)$^+$: 408, 337, 231, 203

35 ml of a tetrahydrofuran solution of 0.8 moles of lithium borohydride was added to a mixture of 10.0 g of the thus obtained product and 100 ml of tetrahydrofuran at −20° C. and agitated for 2 hours. The reaction mixture was poured into dilute sulfuric acid and extracted with methylene chloride. The methylene chloride solution was washed with brine, dried and concentrated, followed by purification through silica gel chromatography to obtain 3.58 g (yield: 39%) of the intended product. The results of IR analysis and measurement of phase transition temperatures are shown below.

IR (liquid film)$v_{max}$: 2924, 2860, 2106, 1759, 1504, 1263, 1225, 1186, 1120, 987, 835 $cm^{-1}$ $T_{CI}$ (crystal phase-isotropic phase transition temperature)=25° C.

EXAMPLE 4

Preparation of (4-cyanophenyl) trans-4-n-pentyl-4-silacyclohexanecarboxylate

The general procedure of Example 3 was repeated using 4-cyanophenol, thereby obtaining the intended product.

EXAMPLE 5

Preparation of (4-chlorophenyl) trans-4-n-pentyl-4-silacyclohexanecarboxylate

The general procedure of Example 3 was repeated using 4-chlorophenol, thereby obtaining the intended product.

EXAMPLE 6

Preparation of (4-cyano-3-fluorophenyl) trans-4-n-pentyl-4-silacyclohexanecarboxylate The general procedure of Example 3 was repeated using 4-cyano-3-fluorophenol, thereby obtaining the intended product.

EXAMPLE 7

Preparation of (4-n-propoxyphenyl) trans-4-n-pentyl-4-silacyclohexanecarboxylate The general procedure of Example 3 was repeated using 4-n-propoxyphenol, thereby obtaining the intended product.

The results of IR analysis and measurement of phase transition temperatures are shown below.

IR (liquid film) $v_{max}$: 2914, 2877, 2089, 1755, 1508, 1198, 1124, 987, 895, 837 cm$^{-1}$ $T_{CN}$ (crystal phase-nematic phase transition temperature) =31° C.

$T_{CI}$ (crystal phase-isotropic phase transition temperature) =55° C.

EXAMPLE 8

Preparation of (4-ethylphenyl) trans-4-n-pentyl-4-silacyclohexanecarboxylate

The general procedure of Example 3 was repeated using 4-ethylphenol, thereby obtaining the intended product.

EXAMPLE 9

Preparation of (4-fluorophenyl) trans-4-n-pentyl-4-silacyclohexanecarboxylate

The general procedure of Example 3 was repeated using 4-fluorophenol, thereby obtaining the intended product. The results of IR analysis and measurement of phase transition temperatures are shown below.

IR (liquid film) $v_{max}$: 2924, 2860, 2104, 1757, 1504, 1188, 1122, 987, 829 cm$^{-1}$ $T_{CN}$ (crystal phase-nematic phase transition temperature) =−21° C.

$T_{CI}$ (crystal phase-isotropic phase transition temperature) =14° C.

EXAMPLE 10

Preparation of (3,4-difluorophenyl) trans-4-n-heptyl-4-silacyclohexanecarboxylate The general procedure of Example 3 was repeated using 3,4-difluorophenol and 4-n-heptyl-4-phenyl-4-silacyclohexanecarboxylic acid, thereby obtaining the intended product.

EXAMPLE 11

Preparation of (4-trifluoromethoxyphenyl) trans-4-n-heptyl-4-silacyclohexanecarboxylate The general procedure of Example 3 was repeated using 4-n-heptyl-4-phenyl-4-silacyclohexanecarboxylic acid, thereby obtaining the intended product.

EXAMPLE 12

Preparation of (4-difluoromethoxyphenyl) trans-4-n-heptyl-4-silacyclohexanecarboxylate The general procedure of Example 3 was repeated using 4-difluoromethoxyphenol and 4-n-heptyl-4-phenyl-4-silacyclohexanecarboxylic acid, thereby obtaining the intended product.

EXAMPLE 13

Preparation of (3-fluoro-4-trifluoromethoxyphenyl) trans-4-n-heptyl-4-silacyclohexanecarboxylate The general procedure of Example 3 was repeated using 3-fluoro-4-trifluoromethoxyphenol and 4-n-heptyl-4-phenyl-4-silacyclohexanecarboxylic acid, thereby obtaining the intended product.

EXAMPLE 14

Preparation of (4-chloro-3-fluorophenyl) trans-4-n-heptyl-4-silacyclohexanecarboxylate The general procedure of Example 3 was repeated using 4-chloro-3-fluorophenol and 4-n-heptyl-4-phenyl-4-silacyclohexanecarboxylic acid, thereby obtaining the intended product.

EXAMPLE 15

Preparation of (3,4,5-trifluorophenyl) trans-4-n-heptyl-4-silacyclohexanecarboxylate The general procedure of Example 3 was repeated using 3,4,5-trifluorophenol and 4-n-heptyl-4-phenyl-4-silacyclohexanecarboxylic acid, thereby obtaining the intended product.

EXAMPLE 16

Preparation of (3,5-difluoro-4-difluoromethoxyphenyl) trans-4-n-heptyl-4-silacyclohexanecarboxylate The general procedure of Example 3 was repeated using 3,5-difluoro-4-difluoromethoxyphenol and 4-n-heptyl-4-phenyl-4-silacyclohexanecarboxylic acid, thereby obtaining the intended product.

EXAMPLE 17

Preparation of (4-fluorophenyl) trans-4-(5-methoxypentyl)-4-silacyclohexanecarboxylate The general procedure of Example 3 was repeated using 4-fluoromthoxyphenol and 4-(5-methoxypentyl)-4-phenyl-4-silacyclohexanecarboxylic acid, thereby obtaining the intended product.

EXAMPLE 18

Preparation of (4-fluorophenyl) trans-4-(4-pentenyl)-4-silacyclohexanecarboxylate The general procedure of Example 3 was repeated using (4-fluorophenol and 4-(4-pentenyl)-4-phenyl-4-silacyclohexanecarboxylic acid, thereby obtaining the intended product.

EXAMPLE 19

Preparation of (4-trifluoromethoxyphenyl) trans-4-(4-fluorobutyl)-4-silacyclohexanecarboxylate The general procedure of Example 3 was repeated using 4-(4-fluorobutyl)-4-phenyl-4-silacyclohexanecarboxylic acid, thereby obtaining the intended product.

EXAMPLE 20

Preparation of (3,4-difluorophenyl) trans-4-(4-fluoropentyl)-4-silacyclohexanecarboxylate The general procedure of Example 3 was repeated using (3,4-difluorophenol and 4-(4-fluoropentyl)-4-phenyl-4-silacyclohexanecarboxylic acid, thereby obtaining the intended product.

EXAMPLE 21

Preparation of (4-cyanophenyl) trans-4-fluoro-4-n-heptyl-4-silacyclohexanecarboxylate The general procedure of Example 3 was repeated except that (4-cyanophenol and 4-n-heptyl-4-phenyl-4- silacyclohexanecarboxylic acid, thereby obtaining the intended product were used and that zinc fluoride was reacted prior to the hydrogenation of the resultant 4-chloro-4-n-heptyl-4- silacylohexanecarboxylate.

EXAMPLE 22

Preparation of (4-ethoxy-2,3-difluorophenyl) trans-4-n-pentyl-4-silacyclohexanecarboxylate The general procedure of Example 3 was repeated using (4-ethoxy-2,3-difluorophenol, thereby obtaining the intended product. The results of IR analysis and measurement of phase transition temperatures are shown below.

IR (liquid film) $v_{max}$: 2924, 2860, 2104, 1767, 1502, 1257, 1155, 1082, 1030, 993, 893, 818 cm$^{-1}$ $T_{CN}$ (crystal phase-nematic phase transition temperature) =221° C.

$T_{CI}$ (crystal phase-isotropic phase transition temperature) =37° C.

EXAMPLE 23

Preparation of (4-cyanophenyl) trans-4-(3-methylbutyl)-4-silacyclohexanecarboxylate The general procedure of Example 3 was repeated using (4-cyanophenol and 4-(3-methylbutyl)-4-phenyl-4-silacyclohexanecarboxylic acid, thereby obtaining the intended product.

EXAMPLE 24

A liquid crystal mixture A was prepared by mixing 40% by mole of 4-(trans-4-(trans-4-ethylcyclohexyl)cyclohexyl)-1,2-difluorobenzene, 35% by mole of 4-(trans-4-(trans-4-propylcyclohexyl))cyclohexyl)-1,2-difluorobenzene, and 25% by mole of 4-(trans-4-(trans-4-pentylcyclohexyl)cyclohexyl)-1,2-difluorobenzene. The mixture had the following characteristic properties.

$V_{th}$ (threshold voltage at 20° C.)=2.45 V

η (viscosity at 20° C.)=25.5 centipoises

A mixed liquid crystal composed of 85% by mole the mixture A and 15% by mole of the (4-fluorophenyl) trans-4-n-heptyl-4-silacyclohexanecarboxylate obtained in Example 9 was prepared. This mixed liquid crystal had the following threshold voltage and viscosity, revealing that the compound of the invention was able to reduce both the threshold voltage and the viscosity.

$V_{th}$ (threshold voltage at 20° C.)=2.20 V

η (viscosity at 20° C.)=21.0 centipoises

EXAMPLE 25

A mixture composed of 85% by mole of the mixture A of Example 24 and 15% by mole of the (4-ethoxy-2,3-difluorophenyl) trans-4-n-pentyl-4-silacyclohexanecarboxylate obtained in Example 22 was prepared. The mixture was found to be effective in reducing a dielectric anisotropy, Δε, and a viscosity, η, as shown below.

| | Mixture A | Mixture comprising the silacylohexanecarboxylate of Example 22 |
|---|---|---|
| Δε (1 KHz, 20° C.) | 4.60 | 3.10 |
| η (viscosity, 20° C.) | 25.5 cps. | 20.0 cps. |

As will be apparent from the foregoing examples, the compounds of the invention are effective in reducing the viscosity and threshold voltage when used as a component or components of liquid crystal compositions. Especially, the compounds of the formula (I) wherein X is an alkyl, alkoxy or alkoxyalkoxy have the function of reducing a dielectric anisotropy, Δε. The reduction of the threshold voltage leads to a low drive voltage of a liquid crystal display device. The lowering of the viscosity brings about a high response speed and the reduction of the dielectric anisotropy results in an improvement of contrast.

What is claimed is:

1. A silacyclohexane compound of the following formula (I)

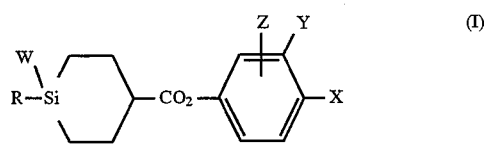

wherein R is selected from the group consisting of a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms and an alkenyl group having from 2 to 8 carbon atoms, W is H, F, Cl or CH$_3$, X is selected from the group consisting of CN, F, Cl, CF$_3$, OCF$_3$, OCF$_2$Cl, OCHFCl, OCHF$_2$, a linear alkyl group having from 1 to 10 carbon atoms, an alkoxy group having from 1 to 10 carbon atoms, an alkoxyalkoxy group having from 2 to 7 carbon atoms, (O)$_l$CY$_1$=CX$_1$X$_2$ wherein l is 0 or 1, Y$_1$ and X$_1$ independently represent H, F or Cl, X$_2$ represents H, F or Cl and O(CH$_2$)$_r$(CF$_2$)$_s$X$_3$ wherein r and 2 are, respectively, 0, 1 or 2 provided that r+s=2, 3 or 4, X$_3$ represents H, F or Cl, and Y and Z, respectively, represent H, F or Cl.

2. A silacyclohexane compound according to claim 1, wherein said compound has a moiety of the following formula

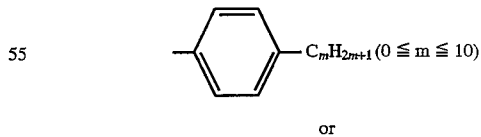

or

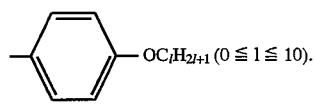

3. A silacyclohexane compound according to claim 1, wherein said compound has a moiety of the following formula

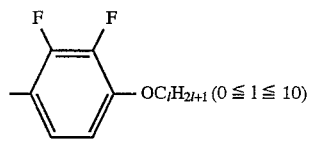

or

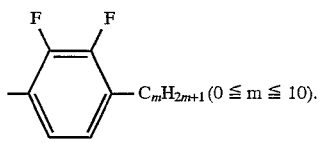

4. A silacyclohexane compound according to claim 1, wherein X is an alkyl group, an alkoxy group or an alkoxyalkoxyl group.

5. A liquid crystal composition comprising at least one silacyclohexane compound of the following formula (I)

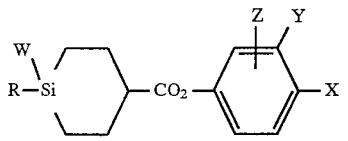

wherein R is selected from the group consisting of a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms and an alkenyl group having from 2 to 8 carbon atoms, W is H, F, Cl or $CH_3$, X is selected from the group consisting of CN, F, Cl, $CF_3$, $OCF_3$, $OCF_2Cl$, $OCHFCl$, $OCHF_2$, a linear alkyl group having from 1 to 10 carbon atoms, an alkoxy group having from 1 to 10 carbon atoms, an alkoxyalkoxy group having from 2 to 7 carbon atoms, $(O)_lCY_1=CX_1X_2$ wherein l is 0 or 1, $Y_1$ and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl, and Y and Z, respectively, represent H, F or Cl.

6. A liquid crystal composition according to claim 5, wherein said at least one silacyclohexane compound is present in an amount of from 1 to 50% by mole.

7. A liquid crystal composition according to claim 5, further comprising at least one compound selected from the group consisting of compounds of the following formulas

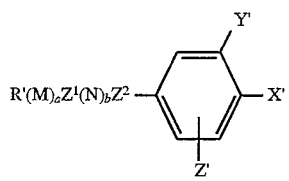

and

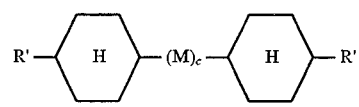

wherein each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms as defined in the afore-indicated formula (I); X' represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY_1=CX_1X_2$ wherein l is 0 or 1, $Y_1$ and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted trans-1,4-cyclohexylene group, (2) a trans-1,4-cyclohexylene group wherein one $CH_2$ unit or two $CH_2$ units, which are not adjacent to each other, of the cyclohexane ring are replaced by O or S, (3) a 1,4-cyclohexenylene group, (4) an unsubstituted or substituted 1,4-phenylene group and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, $-CH_2CH_2-$, $-CH=CH-$, $-C\equiv C-$, $-CO_2-$, $-OCO-$, $-CH_2O-$, $-OCH_2-$ or single bond.

8. A liquid crystal display device comprising the composition defined in claim 5.

* * * * *